US00PP28194P2

(12) United States Plant Patent
Robacker et al.

(10) Patent No.: US PP28,194 P2
(45) Date of Patent: Jul. 11, 2017

(54) GRASS NAMED 'CINNAMON GIRL'

(50) Latin Name: *Schizachyrium scoparium*
Varietal Denomination: Cinnamon Girl

(71) Applicants: University of Georgia Research Foundation, Inc., Athens, GA (US); The United States of America, as Represented by the Secretary of Agriculture, Washington, DC (US)

(72) Inventors: Carol D. Robacker, Peachtree City, GA (US); Melanie L. Harrison, Griffin, GA (US)

(73) Assignees: University of Georgia Research Foundation, Inc., Athens, GA (US); The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/998,813

(22) Filed: Feb. 19, 2016

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Annette Para
(74) *Attorney, Agent, or Firm* — Klarquist Sparkman, LLP

(57) ABSTRACT

The new variety *Schizachyrium scoparium* 'Cinnamon Girl' is tough, adaptable, and drought tolerant; with foliage that is red, purple and green from May to September; with a narrow upright and rounded growth habit; and with foliage that tends to cascade. The asexually reproduced variety is reliably propagated vegetatively.

9 Drawing Sheets

Latin name of the genus and species of the plant claimed: *Schizachyrium scoparium.*

Variety denomination: The new *Schizachyrium scoparium* claimed is of the cultivar denominated 'Cinnamon Girl'.

BACKGROUND OF THE INVENTION

The present invention relates to a new and distinct cultivar of *Schizachyrium scoparium* hereinafter referred to by the varietal domination 'Cinnamon Girl'.

The new *Schizachyrium* is a product of a planned breeding program conducted by the Inventors in Griffin, Ga. The objective of the *Schizachyrium* breeding program is to produce a tough and adaptable drought-tolerant plant with commercial value. This cultivar has significant commercial and home gardener appeal with its attractive foliage and low maintenance requirements. These and other qualities are enumerated herein.

Pedigree and history: In 2006, thirty-seven accessions (number of plants per accession ranged from one to 51 depending upon the germination of individual accessions) of *Schizachyrium scoparium* were germinated and transplanted into field plots in Griffin, Ga. After a two-year evaluation period, seeds from open pollination within accessions were collected and sown in 2008, yielding 368 seedlings. A plant was selected from these seedlings, and was labeled 'B20-28'. Seeds from open pollination were collected from 'B20-28' and were sown in spring 2009. The resulting seedlings were evaluated in containers in the screenhouse for two seasons. The new variety 'B20-28-10', now called 'Cinnamon Girl', was selected from these resulting seedlings and was propagated by root division in 2011 in Griffin, Ga., and planted into a field plot. The new variety 'Cinnamon Girl' has been tested since 2011 in Griffin and Blairsville, Ga.

SUMMARY OF THE INVENTION

The following traits have been repeatedly observed and represent the characteristics of a new variety *Schizachyrium scoparium*, 'Cinnamon Girl'. The new variety 'Cinnamon Girl' has not been observed under all possible environmental conditions. The phenotype may vary somewhat with variations in, for example, temperature, day-length, light intensity, soil types, and water and fertility levels without, however, any variance in genotype.

Asexual reproduction of the new *Schizachyrium* 'Cinnamon Girl' by root division since 2011 has shown that the unique features of this new *Schizachyrium* are stable and reproduced true to type in successive generations.

'Cinnamon Girl' plants, along with the cultivars 'MinnblueA' (U.S. Plant Pat. No. 17,310) and 'Carousel' (U.S. Plant Pat. No. 20,948) have been evaluated for four years in field plots at Griffin, Ga. and Blairsville, Ga. Height from the soil to the tip of the flowering culm, height from the soil to the top of the foliage and width were collected each year from the Griffin plants. Foliage color was assessed monthly from May to September each year.

Throughout this specification, color names beginning with a small letter signify that the name of that color, as used in common speech, is aptly descriptive. Color names beginning with a capital letter designate values based upon The R.H.S. Colour Chart, $5^{th}$ edition published by The Royal Horticultural Society, London, England.

The following traits have been consistently observed in the original plant of this new variety and in asexually propagated progeny grown from root divisions in Blairsville, and Griffin, Ga., and, to the best knowledge of the inventors, their combination forms the unique characteristics of the new variety 'Cinnamon Girl':

1. Foliage of 'Cinnamon Girl' is red, purple and green from May to September.
2. 'Cinnamon Girl' exhibits an upright rounded growth habit.

The new variety *Schizachyrium* 'Cinnamon Girl' can be compared to the little bluestem cultivars 'Carousel' and 'MinnblueA'. Plants of the new 'Cinnamon Girl' variety differ from 'Carousel' and 'MinnblueA' in the following characteristics:

1. The new variety 'Cinnamon Girl' is taller in total height and has a higher average foliage height than both 'Carousel' and 'MinnblueA'.
2. The average canopy diameter of the new variety 'Cinnamon Girl' is narrower than the canopy diameter of 'MinnblueA' and 'Carousel'.
3. The new variety 'Cinnamon Girl' is different from 'Carousel' and 'MinnblueA' in foliage growth. The new variety 'Cinnamon Girl' has cascading foliage, whereas 'Carousel' and 'MinnblueA' have mostly upright pointing foliage.
4. The new variety 'Cinnamon Girl' is different from 'Carousel' and 'MinnblueA' in foliage color. The foliage of the new variety 'Cinnamon Girl' is red, purple, and green throughout the growing season, while the foliage of 'Carousel' and 'MinnblueA' is mostly green to green-blue.

The following observations, measurements, and values describe plants grown in Griffin, Ga. 'Cinnamon Girl' was propagated via root division and grown in one-quart containers prior to planting in field plots. All data are from plants established as single stem propagules in May 2011.

The new variety 'Cinnamon Girl' has colorful red, purple, and green cascading foliage throughout the summer, in contrast to the green to blue-green foliage of 'Carousel' and 'MinnblueA' (Table 1). 'Cinnamon Girl' was on average taller in total height than 'Carousel' and displayed greater foliage height at the test sites in Griffin, Ga. (Table 2). 'MinnblueA' exhibited the greatest foliage width of 'Cinnamon Girl' and 'Carousel' plants (Table 2). The new variety 'Cinnamon Girl' is observed to have a lower plant width to foliage height ratio and a lower plant width to total height ratio than 'Carousel', 'MinnblueA', 'Blaze' (unpatented), 'The Blues' (unpatented) and 'Prairie Blue' (unpatented) (Table 3). The foliage height to total height ratio was observed to be similar between 'Cinnamon Girl', 'Carousel', 'The Blues' and 'Prairie Blues' (Table 3).

At the same age of development and under the same growing conditions, 'Cinnamon Girl' is narrower in width and taller than 'Good Vibrations'; (patent pending); and shorter and narrower in width than 'Seasons in the Sun' (patent pending).

'Seasons in the Sun' and 'Cinnamon Girl' have an upright rounded growth habit with cascading foliage from May to September, but the foliage of 'Good Vibrations' is upright in early summer, changing to cascading in midsummer.

Foliage colors vary during the growing season among these three cultivars. 'Good Vibrations' in early summer has Violet-Blue N92D, 'Seasons in the Sun' has Purple N77A or Purple 79A and 'Cinnamon Girl' has Purple N79C or Greyed-Purple 187A on the distal portion of the foliage. In mid-summer, while all three cultivars have various shades of Greyed-Purple on the distal portion of the leaves, 'Good Vibrations' also has Purple N77C. In late summer, both 'Cinnamon Girl' and 'Good Vibrations' have some Yellow-Green 144A leaves, while 'Seasons in the Sun' has some Green 138B leaves. Furthermore, 'Cinnamon Girl' has some Red-Purple 59A or Red-Purple 60C foliage, colors not seen in the other cultivars.

TABLE 1

Summary of foliage colors on upper leaf surface of 'Cinnamon Girl', 'MinnblueA', and 'Carousel' on Jul. 11, Aug. 4, and Sep. 3, 2014 on field plants in Griffin, GA. Number in parentheses indicates the percentage of leaves displaying primary color.

| Cultivar | Date | Primary Color | Secondary Color |
|---|---|---|---|
| 'Cinnamon Girl' | Jul. | Greyed-purple 187A on upper two-thirds of the leaf (90%) | Green 138A or B, or 137C on lower third of foliage |
| | Aug. | Red-purple 59A or Greyed-Purple 187B or C (90%) | Yellow-Green 144A |
| | Sep. | Greyed-Purple 187A (60%) | Green 138A or 138B |
| 'MinnblueA' | Jul. | Green N138B (80%) on entire leaf | Purple N77A on tips of foliage (20%) |
| | Aug. | Green 137A (100%) | |
| | Sep. | Green 137A (90%) | Greyed-Purple 183B (10%) |
| 'Carousel' | Jul. | Green (100%) | |
| | Aug. | Green 137B (100%) | |
| | Sep. | Green 137A or 138A (100%) | |

TABLE 2

Total height, height to top of foliage and width of 'Cinnamon Girl' and two cultivars planted into a field plot in Griffin, GA. Data were collected on Nov. 20, 2014. Numbers in parentheses are the standard deviations.

| Cultivar | Number of reps | Total height (cm) (soil to tip of flowering stem) | Foliage height (cm) | Width (cm) |
|---|---|---|---|---|
| 'Cinnamon Girl' | 4 | 100 (17.2) | 43.5 (7.6) | 34.6 (9.0) |
| 'MinnblueA' | 4 | 95.0 (10.1) | 36.5 (5.9) | 61 (16.4) |
| 'Carousel' | 4 | 73.8 (17) | 24.5 (9.8) | 43.5 (9.7) |

In Table 2, total plant heights were measured from ground level to the tip of the highest flowering culm. Foliage width was measure twice on each plant, the first measurement being at the widest point and the second measurement perpendicular to the first. These measurements were made on Nov. 20, 2014, in Griffin, Ga. after four growing seasons. All measurements are in cm.

TABLE 3

Relationship of plant width to foliage height, plant width to total height and foliage height to total height of 'Cinnamon Girl' and five cultivars planted into a field plot in Griffin, GA. Measurements were made on Nov. 20, 2014 on four reps of 'Cinnamon Girl', 'MinnblueA', and 'Carousel', and one plant each of 'Blaze', 'The Blues', and 'Prairie Blues'. Numbers in parentheses are the standard deviations.

| Cultivar | Plant width/ Foliage height | Plant width/ Total height | Foliage height/ Total height |
|---|---|---|---|
| 'Cinnamon Girl' | 1.07 (0.31) | 0.38 (0.07) | 0.34 (0.04) |
| 'MinnblueA' | 3.32 (0.49) | 0.85 (0.16) | 0.26 (.02) |
| 'Carousel' | 2.74 (0.86) | 0.87 (0.19) | 0.33 (0.1) |
| 'Blaze' | 2.44 | 0.51 | 0.21 |
| 'The Blues' | 1.52 | 0.52 | 0.34 |
| 'Prairie Blues' | 2.17 | 0.51 | 0.24 |

In Table 3, the relationship between foliage height and plant width is presented.

In summary, 'Cinnamon Girl' has cascading foliage and more varied foliage color than 'Carousel' and 'MinnblueA'. 'Cinnamon Girl' is taller than both 'Carousel' and 'MinnblueA' in foliage height. 'Cinnamon Girl' and 'Carousel' are narrower than 'MinnblueA' in foliage width. 'Cinnamon Girl' is upright and rounded, with foliage height exceeding width, while both 'Carousel' and 'MinnblueA' are broadly rounded, displaying width greater than foliage height.

BRIEF DESCRIPTION OF THE FIGURES

The accompanying colored photographs illustrate the overall appearance and distinct characteristics of the new variety of *Schizachyrium scoparium* 'Cinnamon Girl'. The colors in the photographs are as close as possible with the photographic and printing technology utilized.

FIGS. 4 and 5 are photographs of a 'Cinnamon Girl' plant taken on Jun. 8, 2012 in Griffin, Ga.; with FIG. 5 being an enlarged view.

FIGS. 8 and 9 are, respectively, photographs of a 'Cinnamon Girl' plant taken on Jul. 1, 2015, in Griffin, Ga.; with FIG. 9 being an enlarged view.

FIGS. 10 and 11 are, respectively, photographs of a 'Carousel' plant (FIG. 10) and a 'MinnblueA' plant (FIG. 11) taken on Jul. 1, 2015, in Griffin, Ga.

FIGS. 14 and 15, respectively, are photographs of 'Carousel' (FIG. 14) and 'MinnblueA' (FIG. 15) plants, taken on Aug. 22, 2012, in Griffin, Ga.

FIGS. 16 and 17 are photographs of a 'Cinnamon Girl' plant taken on Sep. 10, 2014, in Griffin, Ga.; with FIG. 17 being an enlarged view.

FIGS. 18 and 19 are, respectively, photographs of 'Carousel' (FIG. 18) and 'MinnblueA' (FIG. 19) plants, taken Sep. 10, 2014, in Griffin, Ga.

BOTANICAL DESCRIPTION

Figure 1:
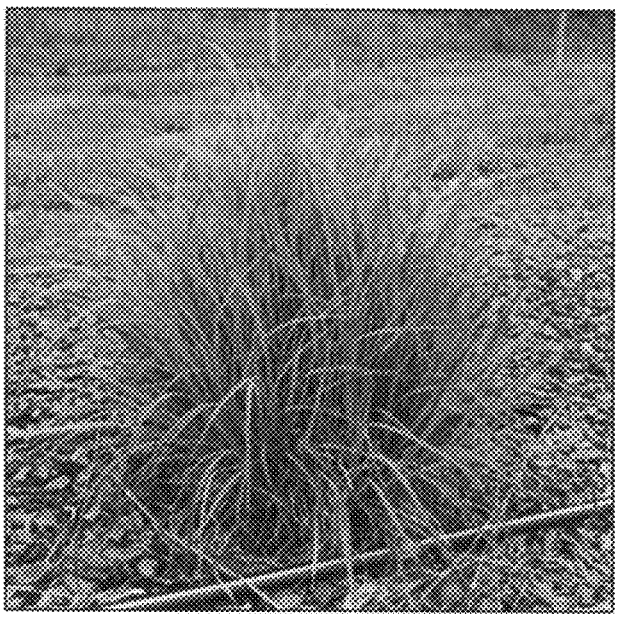
FIG. 1 is a photograph of a plant of the new variety 'Cinnamon Girl' taken on May 26, 2015 in Griffin, Ga.
Figure 2:
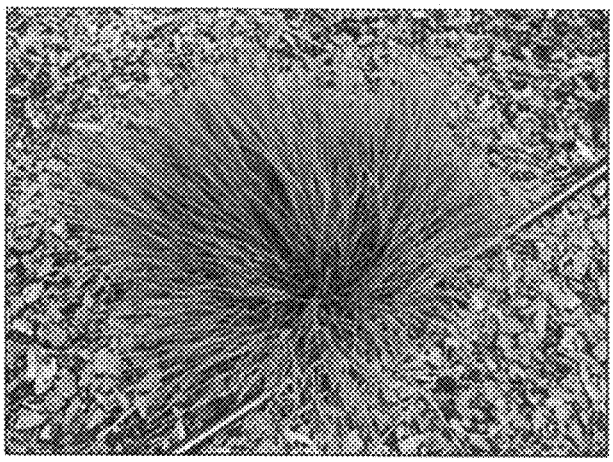
FIGS. 2 and 3 are, respectively, photographs of a 'Carousel' plant (FIG. 2) and of a 'MinnblueA' plant (FIG. 3), taken on May 26, 2015 in Griffin, Ga.
Figure 3:
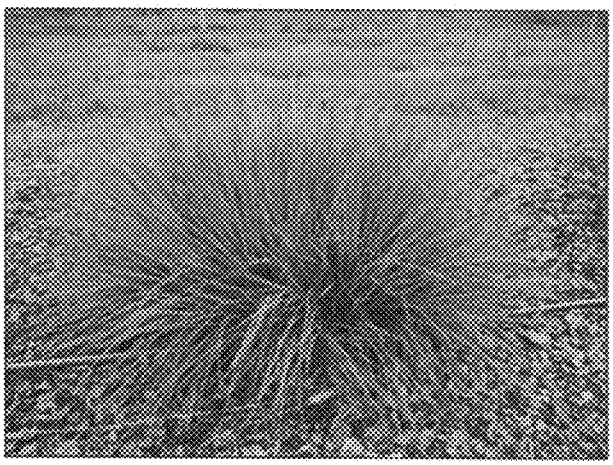
Figure 6:
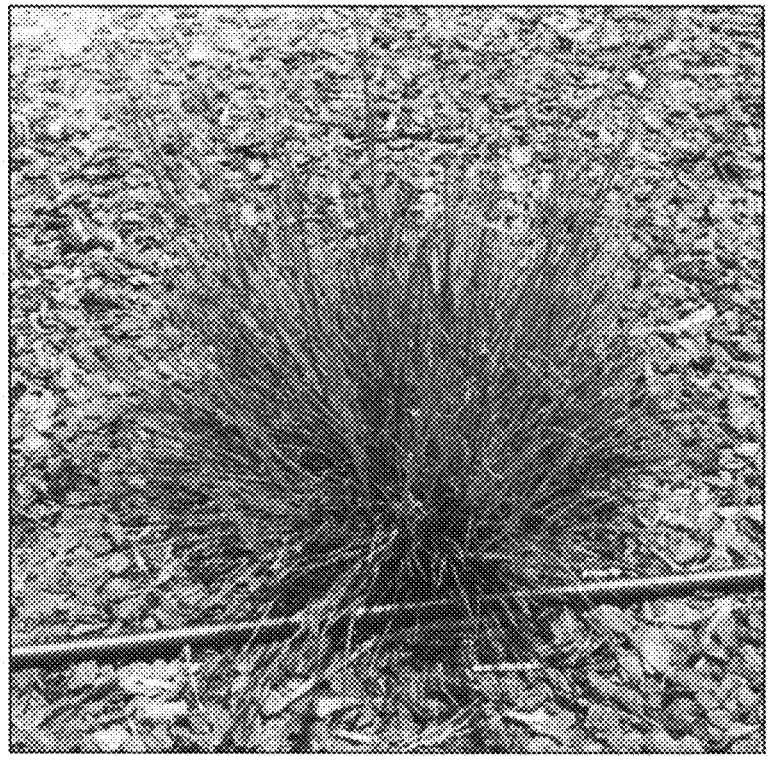
FIGS. 6 and 7 are, respectively, photographs of a 'Carousel' plant (FIG. 6) and a 'MinnblueA' plant (FIG. 7) taken on Jun. 8, 2012 in Griffin, Ga.
Figure 7:
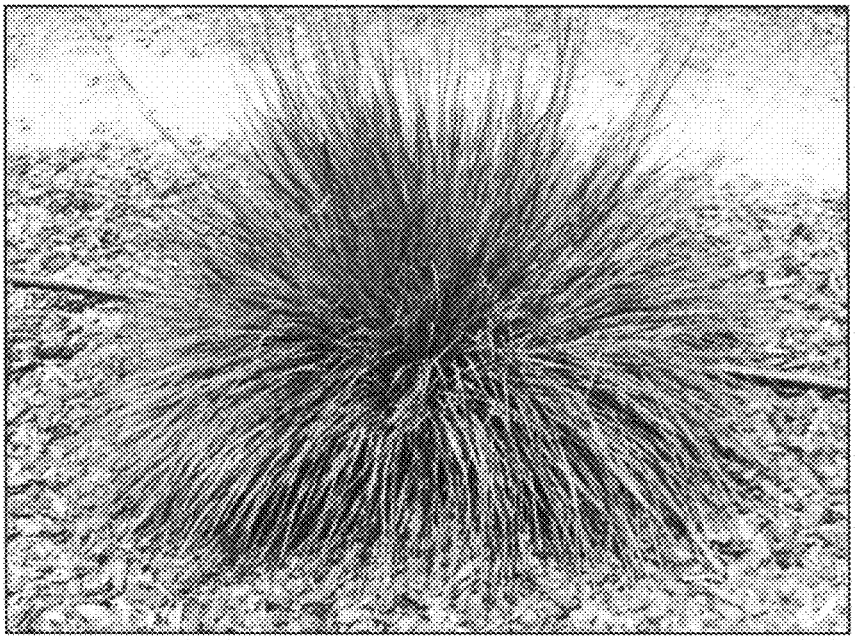
Figure 12:
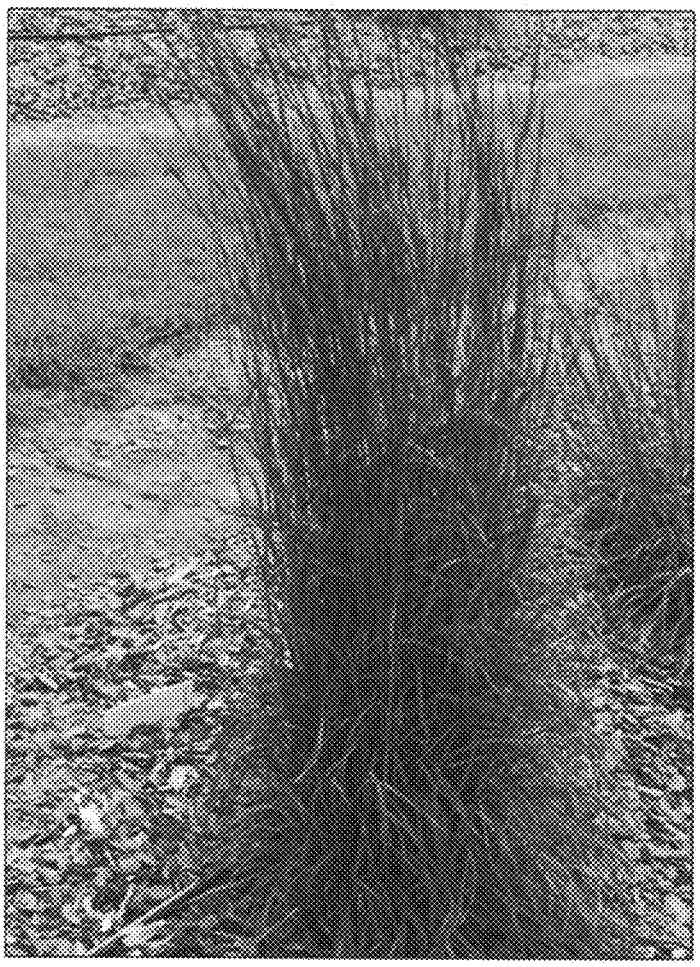
FIGS. 12 and 13 are photographs of a 'Cinnamon Girl' plant taken on Aug. 22, 2012 in Griffin, Ga.; with FIG. 13 being an enlarged view.
Figure 13:
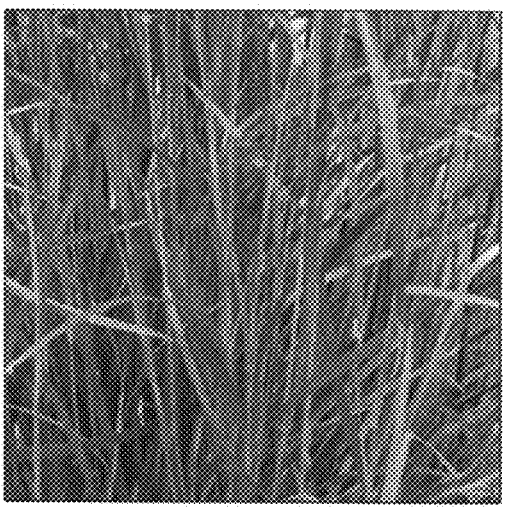

The new variety 'Cinnamon Girl' is a perennial at Griffin, Ga. (USDA Zone 7b). The new variety 'Cinnamon Girl' blooms from mid to late August. 'Cinnamon Girl' is drought tolerant and expected to be able to be grown in USDA Zones 3-9. 'Cinnamon Girl' grows well in full sun and in most soils. 'Cinnamon Girl' is genetically stable and has been propagated by root division. The reproductive organs of the new variety 'Cinnamon Girl' are very small, fleeting or scarce in presence and therefore difficult to describe.

All data are from four-year-old field-grown plants established as single stem propagules in May 2011, in Griffin, Ga. Three replicated plants were grown in a randomized block design.

Plant:

*Mature plant height.*—Approximately 94 to 123 cm.

*Diameter of plant canopy.*—Approximately 33 to 48 cm.

*Foliage height.*—Approximately 48 to 50 cm.

Leaf:

*Leaf shape.*—Linear.

*Leaf division.*—Simple.

*Leaf margins.*—Entire.

*Leaf base.*—Sheathed to base of culm.

*Leaf venation.*—Parallel.

*Leaf apex.*—Acute.

*Leaf arrangement.*—Alternate, 2-ranked.

*Leaf collar type.*—Continuous.

*Leaf persistence.*—Dries but persistent through winter.

*Leaf attachment.*—Sheathed, 1 mm wide membranous ligule.

*Leaf width.*—Approximately 4.4 mm at base and 4.6 mm on blade.

*Leaf length.*—Approximately 25 cm.

*Leaf number.*—5 to 10 leaves per culm.

*Leaf surface.*—Strigillose, not waxy, with villous sheathes.

*Adaxial leaf surface trichomes.*—None.

*Abaxial leaf surface trichomes.*—None.

*Sheath trichomes.*—None.

*Adaxial leaf color.*—Early Summer: Green 138A, Purple N79C or Greyed-Purple 187A. Mid-Summer: Basal portion of the leaf is Green 137C, 138A or 138B, changing to Greyed-Purple N186C, or 187A on the distal portion. Late Summer (displays a mix of color types): Yellow-Green 144A changing to Red-Purple 60C, or Red-Purple 59A, Greyed-Purple 187B, or Greyed-Purple 183C, or Yellow-Green 144A. Early Fall: Green 138B changing to Greyed-Purple 187A, or Greyed-Purple 187A, or Green 138A.

*Abaxial leaf color.*—Early Summer: Green 138B or Mid-Summer: Green 138B. Later Summer (displays a mix of color type): Green 143B, or Greyed-Orange 176A, or Greyed-Purple 183D, Greyed-Purple 183D, or Yellow-Green 144A. Early Fall: Greyed-Green 191A changing to Greyed-Purple 183D, or Greyed-Red 182B, or Green 138A.

Flower:

*Blooming period.*—Mid to late August in Griffin, Ga. with multiple racemes present per flower culm.

*Inflorescence.*—Yes.

*Inflorescence type.*—Racemes at terminus and nodes.

*Inflorescence size.*—2 to 5 cm in length, 0.5 cm in diameter.

*Inflorescence color.*—Red-Purple 59B.

*Spikelet number.*—5 to 8 per raceme.

*Spikelet size.*—3 to 4 cm long and with an internode distance of 1 to 2 cm.

*Spikelet arrangement.*—Alternately on the rachis.

*Spikelet hairs.*—Approximately 1 mm long, White N155D with a fluffy texture.

*Glumes.*—Average of 5 mm long by 1 mm wide.

*Palea.*—2 mm long and less than 1 mm wide.

*Peduncle.*—1 to 9 cm long and 0.5 mm diameter.

*Peduncle color.*—Greyed-Orange 174A.

Culm:

*General.*—Flat, solid.

*Stem surface.*—Strigillose, less toward the base, becoming more numerous on the blade.

*Pith.*—1 mm wide, Yellow-Green 153C.

*Culm color.*—Red-Purple 70C toward the base, changing to Yellow-Green 145A.

*Culm size.*—5 mm diameter and 6 to 8 cm in length before the blade emerges; at blooming, up to 123 cm from the base to the tip of the flower panicle.

*Internode length.*—9 cm.

What is claimed is:

1. A new and distinct variety of the *Schizachyrium* plant named 'Cinnamon Girl' as herein illustrated and described.

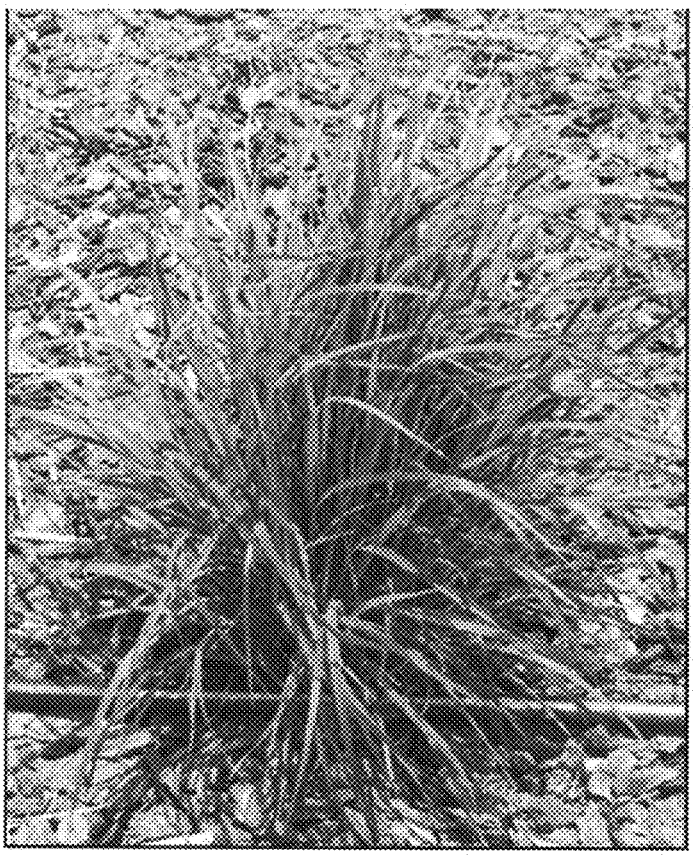
FIG. 4
FIG. 5
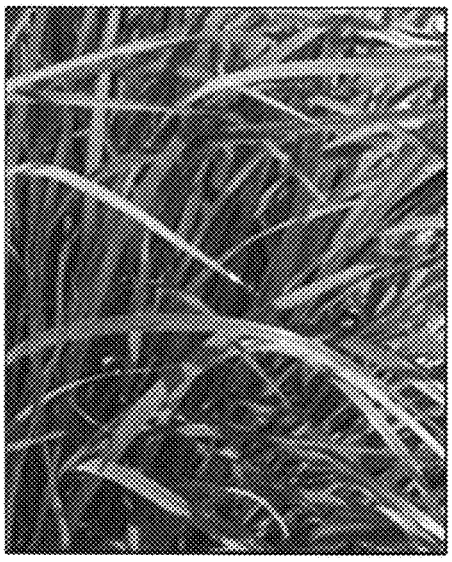

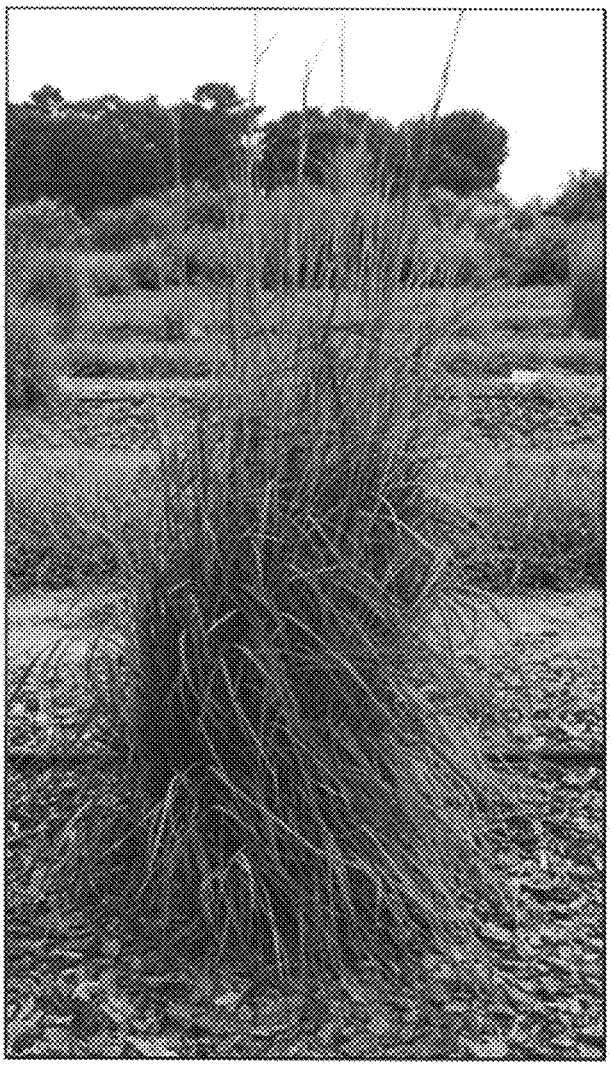
FIG. 8
FIG. 9
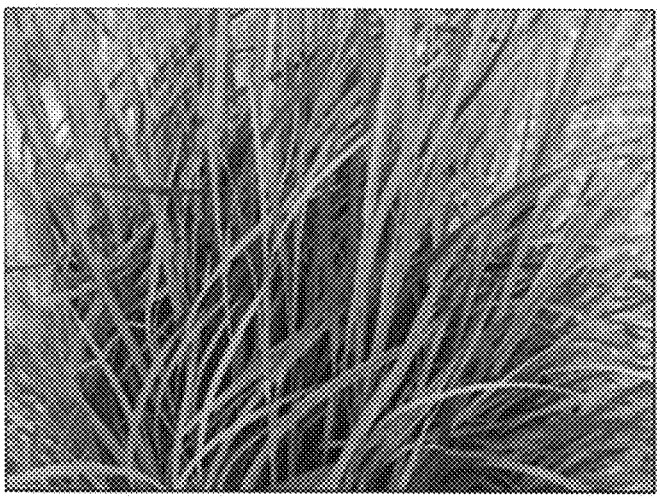

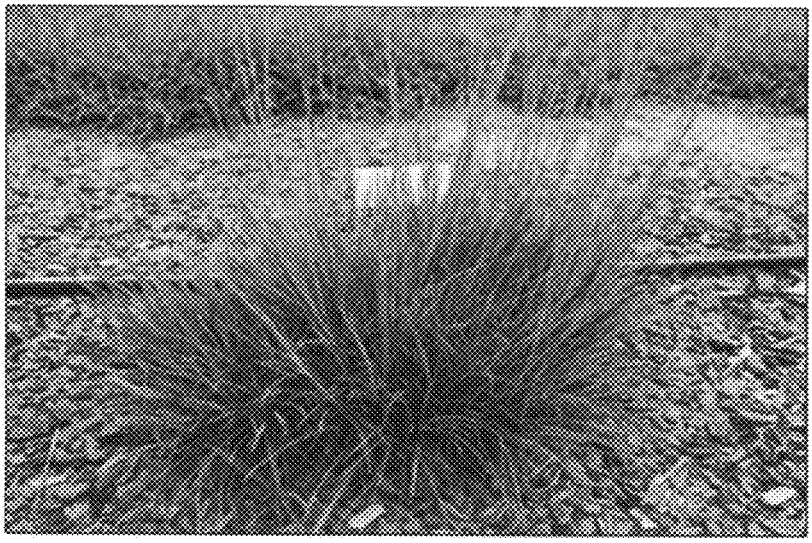
FIG. 10
FIG. 11
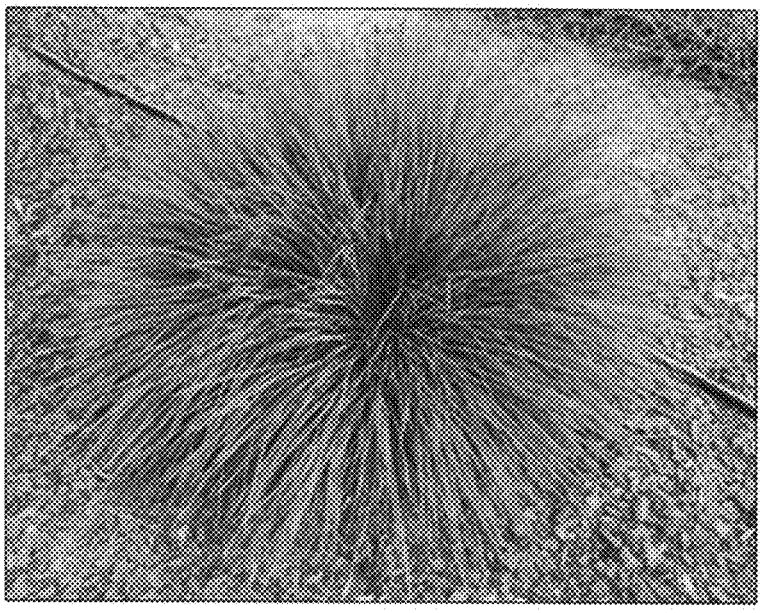

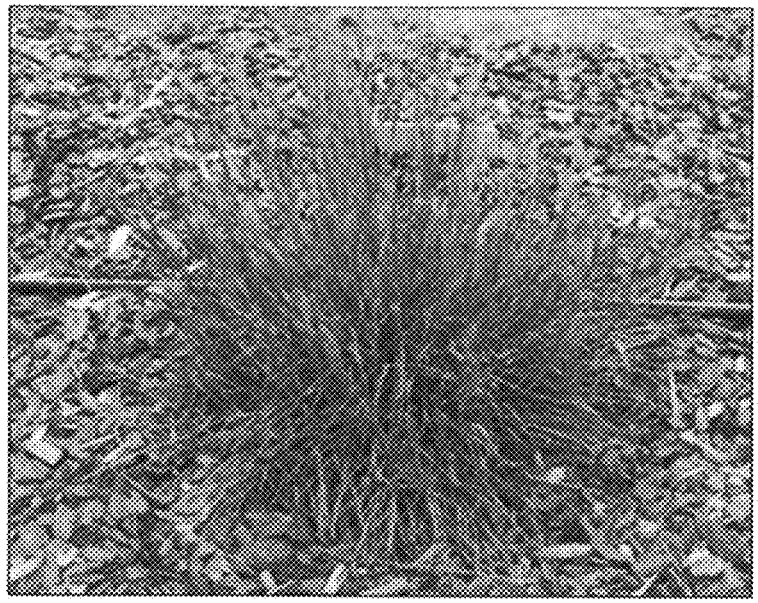
FIG. 14
FIG. 15
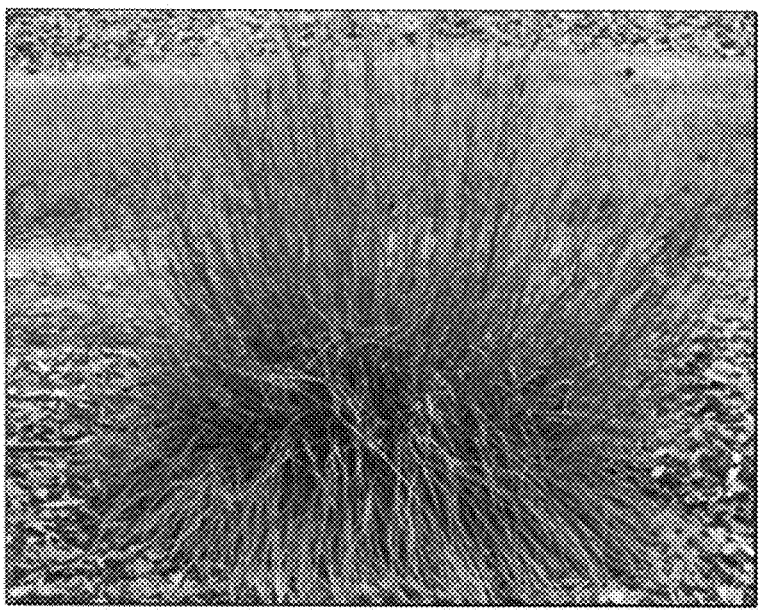

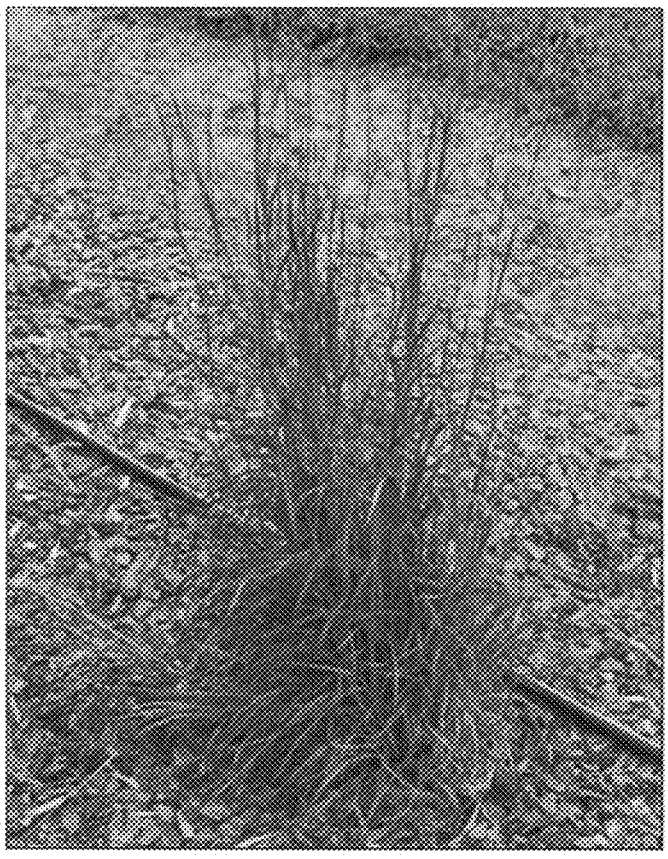
FIG. 16
FIG. 17
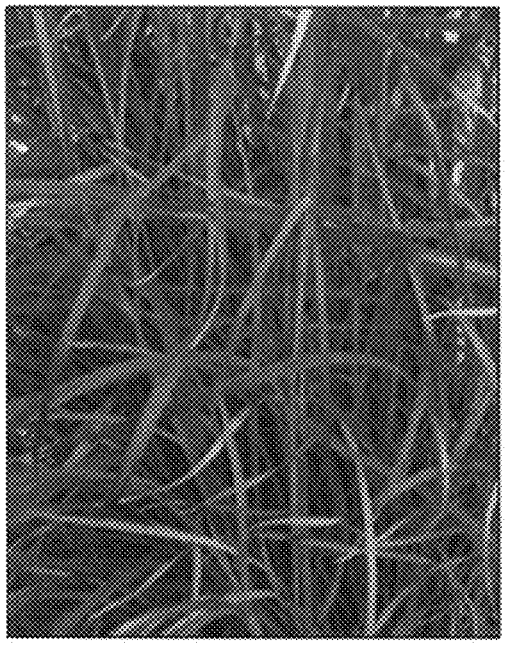

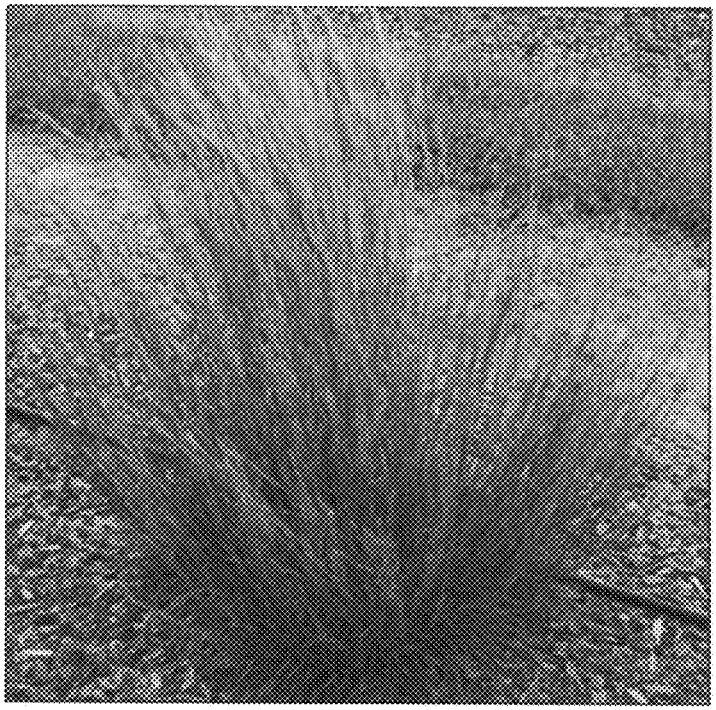
FIG. 18
FIG. 19
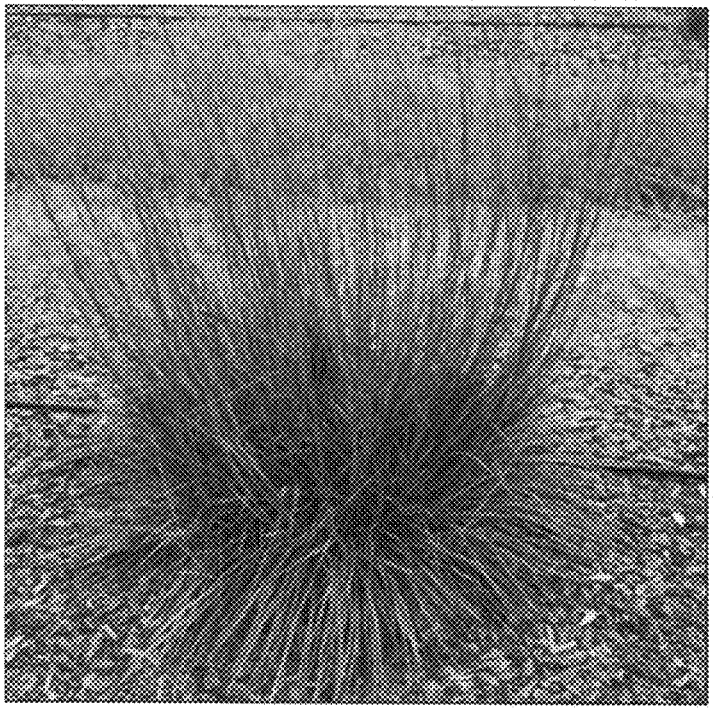

* * * * *